United States Patent
Yamaguchi et al.

(10) Patent No.: US 7,534,485 B2
(45) Date of Patent: May 19, 2009

(54) BUILDING BOARD

(75) Inventors: Takahiro Yamaguchi, Nagoya (JP); Toshio Imai, Yokosuka (JP)

(73) Assignee: Nichiha Corporation, Nagoya-Shi (JP)

( * ) Notice: Subject to any disclaimer, the term of this patent is extended or adjusted under 35 U.S.C. 154(b) by 0 days.

(21) Appl. No.: 11/902,015

(22) Filed: Sep. 18, 2007

(65) Prior Publication Data
US 2008/0233160 A1 Sep. 25, 2008

(30) Foreign Application Priority Data
Mar. 20, 2007 (JP) ............................. 2007-072855

(51) Int. Cl.
*B32B 25/02* (2006.01)
(52) U.S. Cl. .................... 428/297.1; 428/212; 424/409
(58) Field of Classification Search ................ 428/212, 428/297.1, 447, 446, 294.7; 424/409
See application file for complete search history.

(56) References Cited

U.S. PATENT DOCUMENTS

| | | | | |
|---|---|---|---|---|
| 4,258,102 A | * | 3/1981 | Traver et al. ................ 428/331 |
| 5,902,851 A | * | 5/1999 | Yamaki et al. ............... 524/506 |
| 6,025,077 A | * | 2/2000 | Yamaki et al. ............... 428/447 |
| 6,165,619 A | * | 12/2000 | Ikenaga et al. ............... 428/448 |
| 6,281,284 B1 | * | 8/2001 | Sakamoto et al. ........... 524/785 |
| 6,303,229 B2 | * | 10/2001 | Takahama et al. ........... 428/447 |
| 6,309,708 B1 | * | 10/2001 | Mohri et al. ................ 427/387 |
| 6,620,487 B1 | * | 9/2003 | Tonyan et al. ............... 428/192 |
| RE38,850 E | * | 10/2005 | Ikenaga et al. ............... 428/448 |
| 2001/0008696 A1 | * | 7/2001 | Takahama et al. ........... 428/446 |
| 2005/0155731 A1 | * | 7/2005 | Martin et al. ................ 162/158 |
| 2006/0008496 A1 | * | 1/2006 | Kulkarni et al. ............. 424/412 |
| 2006/0054053 A1 | * | 3/2006 | Masutani et al. ............... 106/2 |
| 2006/0068186 A1 | * | 3/2006 | Leclercq et al. ........... 428/294.7 |
| 2008/0233160 A1 | * | 9/2008 | Yamaguchi et al. ......... 424/409 |

FOREIGN PATENT DOCUMENTS

| | | |
|---|---|---|
| JP | 9-235491 A | 9/1997 |
| JP | 2002-338943 A | 11/2002 |

* cited by examiner

*Primary Examiner*—N. Edwards
(74) *Attorney, Agent, or Firm*—Birch, Stewart, Kolasch & Birch, LLP

(57) ABSTRACT

Provided is a functional building board having an antimicrobial function, which retains anti-algal and antifungal agents for a long period of time in a coat on an external wall material by using several kinds of antimicrobial composite materials, and is provided with stain-proofing function to wash away stains on the external wall material, and in which the design is not largely restricted by the color of the anti-algal or antifungal paint or by the state of the coat and the design is not influenced by the coating step in the final step.

The building board according to the present invention has a coat formed on the surface, and is characterized in that antimicrobial composite materials are included on the surface of the coat and a coat layer containing colloidal silica as a main component is formed, said antimicrobial composite materials being characterized in that they control generation of algae and fungi and said building board being a fiber reinforced cement board.

9 Claims, No Drawings

BUILDING BOARD

BACKGROUND OF THE INVENTION

1. Field of the Invention

The present invention relates to a building board having an anti-algal and antifungal function.

2. Description of the Prior Art

Hitherto, surfaces of external wall materials used for the external walls of buildings such as housings have been coated to protect habitants from weather, light and heat. However, it is not possible to avoid deterioration or inconvenient phenomena such as discoloration, chalking, staining, biotic contamination or the like on the surfaces of external wall materials with aging. Recently, on the other hand, the weather-resistant ability of paints has been considerably improved, and spoil of beauty by the biotic contamination with algae or fungi rather than inconvenience caused by discoloration or chalking has become a serious problem. Such biotic contamination does not occur on the whole surfaces of external wall materials but does predominantly on only a part the wall material (mainly on the northern surface) which does not get sun and is high in temperature and humidity, and thus is humid and suitable for growth of algae and fungi.

Hitherto, biotic contamination occurred on a part of external wall materials has to be dealt with recoating on a large-scale or with washing. Specifically, when the part having biotic contamination is washed, a dilute solution of anti-algal agent or antifungal agent has been sprayed to delay reoccurrence of the biotic contamination. However, such agent is merely temporarily retained, and after washing away of the agent by rain, anti-algal and antifungal effects could not be expected. In addition, the kinds of algae and fungi amount to several hundreds and the kinds of algae and fungi that generate in housings amount to twenty to thirty. Thus, there has not been an agent which is effective for all kinds of algae and fungi. Accordingly, many kinds of agents had to be used, which was not economical. In addition, external wall materials are subjected to dust, weather and ultraviolet rays to result in the staining of the surfaces thereof, and the extraneous matter of this stain resulted in generation of algae and fungi.

Meanwhile, a method for providing an anti-algal effect includes a method of adding an anti-algal agent in a paint (for example, JP 9-235491 A), and a method for providing stain-proofing effect to external wall materials includes a method of applying a paint which comprises silica fine particles, alumina fine particles and/or aluminum magnesium complex oxide fine particles to the surface thereof for the purpose of making the surface hydrophilic (for example, JP 2002-338943 A).

SUMMARY OF THE INVENTION

The present invention was made in view of such actual state, and aims to provide a building board which can exhibit anti-algal and anti-fungal functions and is provided with stain-proofing function. Moreover, the present invention aims to provide a method for stably producing such building board.

In order to achieve the purposes, the invention described in claim 1 is a building board which has a coat containing colloidal silica as a main component and an antimicrobial composite material, said coat being formed on the board. The invention described in claim 2 is the building board according to claim 1, wherein the antimicrobial composite material has a function to control generation of algae and fungi. The building board according to claim 1 or 2 is a fiber reinforced cement board. The invention is a method for producing a building board which comprises a first step comprising adding a surfactant to a mixed solvent consisting of water and an alcohol and then dispersing therein colloidal silica to give a first processing liquid, a second step comprising adding to the first processing liquid obtained in the first step an antimicrobial composite material to give a second processing liquid, a third step comprising applying the second processing liquid obtained in the second step to the surface of a building board which has preliminarily been coated, and a fourth step comprising drying the building board obtained in the third step to form a surface coat.

[Action]

The second processing liquid used in such manufacturing method according to the invention is obtained by adding an antimicrobial composite material to an aqueous dispersion of colloidal silica and thus does not contain a paint or the like which contains a resin as a main component, whereby the antimicrobial composite material is fixed to fine convexoconcaves on the surface of the colloidal silica without being hindered by the resin and the colloidal silica is fixed to the coat on the substrate via hydrogen bonding.

[Effect]

As the results, the antimicrobial composite material exists at a high concentration on the surface of the coat on the building board via colloidal silica as a medium and thus the control effect of the antimicrobial composite material is efficiently exhibited to give a functional building board having a high control effect even if only a small amount of the antimicrobial composite material is used. In addition, since the antimicrobial composite material is firmly fixed to the coated surface via colloidal silica as a medium, a lasting control effect of the antimicrobial composite material can be obtained. Moreover, with regard to stain-proofing effect, super hydrophilic property is imparted to the surface which is firmly covered with silica fine particles, and upon contacting with water, self-cleaning function is exhibited, wherein the silica fine particles absorb the water and stains adhered to the surface float and are washed away together with the water. Furthermore, because of super fine particles, the surface remains transparent and the design of the surface is not impaired.

DETAILED DESCRIPTION OF THE INVENTION

The present invention will be explained below in detail.

[Substrate]

The substrate of the building board according to the invention may be a cement board (fiber reinforced cement board) incorporated with a woody reinforcement such as wood flake, woody pulp, wood fiber or pulp, extrusion molded cement board, pulp cement board, gypsum board, calcium silicate board, magnesium carbonate board, cement board, or the like.

[Coating]

The surface of the above substrate is subjected to coating, and specifically, multiple-ply coating comprising undercoating, intermediate coating, top coating, and clear coating. It is desirable to use an aqueous emulsion-type coating composition such as an aqueous acrylic resin emulsion-type coating composition or an aqueous silicone-acrylic resin emulsion-type coating composition for the undercoating, intermediate coating, top coating, and clear coating. However, it is possible to use a solvent-type coating composition such as acrylic resin solvent-type clear coating composition or a combination of an aqueous emulsion-type coating composition and a solvent-type coating composition.

[Antimicrobial Composite Material]

As the components of the antimicrobial composite material is used a mixture of two or more kinds of organic antimicrobial agents and one or more kinds of inorganic antimicrobial agents. Examples of the organic antimicrobial agent include nitrile-based antimicrobial agents, pyridine-based antimicrobial agents, haloalkylthio antimicrobial agents, organic iodide-based antimicrobial agents, thiazole-based antimicrobial agents, benzimidazole-based antimicrobial agents, and imidazole-based organic antimicrobial agents. Examples of the inorganic antimicrobial agent include crystalline silver and sodium aluminosilicates (silver-substituted zeolite), silver/zinc zeolite, silver/zeolite, zirconium phosphate, silver oxide-zirconium phosphate, silver oxide, silver-supported zirconium phosphate, zinc oxide, titanium phosphate, a gel mixture of zinc oxide and titanium oxide, a mixture of silver titanium phosphate-supported gel and zinc oxide, silver-supported silicon dioxide, silver oxide, a mixture of ammonium triphosphate and sodium phosphate, silver chloride, silver, copper, copper compounds, tetraaminecopper ion, phosphate glass, and a hydrophilic aminosilicon polymer containing metal oxides.

A preferred antimicrobial composition contains two kinds of imidazole-based organic antimicrobial agents and an inorganic antimicrobial agent. As the organic antimicrobial agent may be used 2-(4-thiazolyl)-1H-benzimidazole and 2-benzimidazole carbamic acid methyl ester, and as the inorganic antimicrobial agent may be used silver-supported zirconium phosphate and zinc oxide. It is also possible to use calcium oxide obtained by heating shells at a temperature not lower than 800° C., powder of tea leaves or powder of tea dregs.

Among these, may be used imidazole-based organic antimicrobial agents such as benzimidazole carbamic acid compounds, sulfur-containing benzimidazole compounds, and cyclic compound derivatives of benzimidazole.

As the benzimidazole carbamic acid compounds may be used methyl 1H-2-benzimidazole carbamate, methyl 1-butyl-carbamoly-2-benzimidazole carbamate, methyl 6-benzoyl-1H-2-benzimidazole carbamate, and methyl 6-(2-thiphenecarbonyl)-1H-2-benzimidazole carbamate. As the sulfur-containing benzimidazole compounds may be used 1H-2-thiocyanomethylthiobenzimidazole, and 1-dimethylaminosulfonyl-2-cyano-4-bromo-6-trifluoromethyl-benzimidazole. As the cyclic compound derivatives of benzimidazole may be used 2-(4-thiazolyl)-1H-benzimidazole, 2-(2-chlorophenyl)-1H-benzimidazole, 2-(1-(3,5-dimethylpyrazolyl)-1H-benzimidazole, and 2-(2-furyl)-1H-benzimidazole.

As the imidazole-based organic antimicrobial agents, a combination of at least two selected only from imidazole-based organic antimicrobial agents are used. By using two different imidazole-based antimicrobial agents, a synergistic effect of antimicrobial action against microorganisms can be obtained. Particularly, combined use of a compound which has a thiazolyl group on a benzimidazole ring and a compound which has a carbamate group on a benzimidazole ring is preferable because a remarkable synergistic effect is obtainable.

As the thiazolyl group can be used, for example, 2-thiazolyl, 4-thiazolyl, or 5-thiazolyl. As the carbamate group, preferred are those in which the hydrocarbon group in the carbamate group is an alkyl group such as, for example, methyl, ethyl,n-propyl, or iso-propyl, particularly methyl or ethyl. Specifically, as the thiazolyl group-containing compound can be used 2-(4-thiazolyl)-1H-benzimidazole (thiabendazole (TBZ)). As the carbamate group-containing compound can be used methyl-2-benzimidazole carbamate (Carbendazim (BCM)), or ethyl-2-benzimidazole carbamate. Particularly, 2-(4-thiazolyl)-1H-benzimidazole and methyl-2-benzimidazole carbamate are preferred because they are comparatively high in thermal stability, easy to use as a resin molded product and have been used, for example, as a fungicidal agent (food additive) for grape fruit, orange and banana and have been confirmed to have a relatively low effect on human body.

On the other hand, as the inorganic antimicrobial agent, particularly zirconium phosphate carrying silver or copper as a metal is preferred, with zirconium phosphate carrying silver, i.e. a silver-based antimicrobial agent having a high antimicrobial property, being more preferred. Incidentally, the silver-based antimicrobial agent is not restricted to supported forms and includes silver in the form of elementary metal. Zirconium phosphates or zeolites carrying a metal such as silver or copper are preferred because they are excellent in safety to human body, high in antimicrobial rate and excellent in antimicrobial performance, and can reduce the cost since a noble metal such as silver is supported on zirconium phosphates or zeolites.

Particularly when a silver-supported zirconium phosphate or zeolite is used, it is more preferred to use it in combination with zinc oxide. The combined use of a silver-supported zirconium phosphate and zinc oxide is preferred because not only the antimicrobial actions brought about by the silver-supported zirconium phosphate and zinc oxide, but also a synergistic effect of antimicrobial action is obtained even by the combined use of inorganic antimicrobial agents of the same inorganic compounds, whereby giving a more remarkable antimicrobial effect. Moreover, the use in combination with zinc oxide is preferred because the content of a silver-supported zirconium phosphate or zeolite can be reduced, and thus the cost can be readily reduced owing to the reduction of the amount of the noble metal, i.e. silver, used. Furthermore, discoloration due to oxidation of silver can be prevented.

Examples of shells include shells of scallop, little clam, clam, oyster, top shell, abalone and moule. Among these, shells of scallop and oyster which are relatively frequently subjected to industrial treatment are suitable in view of availability, and shells of scallop are suitable in view of low impurity content and effective utilization of a large amount of waste materials. Calcium oxides obtained by baking shells are suitable in view of providing antimicrobial property because they contain trace metals such as zinc, iron and magnesium. Baking of shells is effected at a temperature between 800° C. and 1300° C. for 3 to 6 hours after washing the shells with water. After baking, fine sands or the like are removed from the baked product, and the baked product is incorporated with water to hydrate calcium oxide. After hydration, the product is cooled to about 5 to 40° C. to give a precipitate, then the precipitate is separated by means of a centrifugal separator or filter, and the resulting separated substance is dried and classified to give a calcium oxide hydrate having a predetermined average particle size. It is important to effect the above-mentioned baking at a high temperature in view of enhancing deodorizing and antimicrobial performance of the resulting calcium oxides. If the baking temperature is lower than 800° C., baking may be insufficient and lowers the deodorizing and antimicrobial performance. The baking temperature higher than 1300° C. does not necessarily further enhance the deodorizing and antimicrobial performance but may result in loss of energy consumption. Baking conditions are preferably a temperature of from 900 to 1200° C. and a period of from 3 to 5 hours. It is preferable to pulverize the baked product into not more than 100 μm in particle size after removing sands or the like from the product. A ball mill or jet mill can be used for the pulverization. The amount of water added during the hydration is preferably 0.2 to 1 liter per kg of the baked product.

Powder of tea leaves or powder of tea dregs can be obtained by pulverizing the tea leaves or tea dregs with a ball mill or jet mill after drying them. These powders have an average particle size of preferably 1 to 40 μm and more preferably 5 to 35 μm in view of enhancing dispersibility, as well as deodorizing and antimicrobial properties. Adjustment of the average particle size of the powder of tea leaves or the powder of tea dregs can be effected similarly to the adjustment of the average particle size of the powder of the calcium oxide hydrates.

[Dispersion of Colloidal Silica]

The colloidal silica used in the processing liquid of the present invention is secondary fine particles which were formed by association of about ten primary fine particles having a particle size of 5 to 10 nm, has fine convexoconcaves formed on the surface, and may contain a slight amount of other components such as aluminum oxide in addition to silicon oxide. The colloidal silica exhibits hydrophilic property due to OH radicals. It is believed that the antimicrobial composite material is adsorbed in and fixed to the gaps formed between the secondary particles. The colloidal silica may also contain slight amounts of silicon compounds or silicates such as sodium silicate, potassium silicate, and lithium silicate as a binder.

[Alcohol]

It is desirable to add an alcohol to water as a dispersing medium of the colloidal silica. As the alcohol to be used, a water-soluble alcohol such as methanol, ethanol or isopropanol is desirable. The alcohol lowers the surface tension of the processing liquid and increases the affinity thereof with an underlying coat to increase the wettability of the processing liquid.

[Surfactant]

It is desirable to add a surfactant as a dispersing agent to a dispersing liquid of the colloidal silica. As the surfactant may be used any of usual anionic, nonionic and cationic surfactants. Examples of the anionic surfactants include higher alcohol sulfates (Na salts or amine salts), alkylally sulfonates (Na salts or amine salts), alkylnaphthalene sulfonates (Na salts or amine salts), condensates of alkylnaphthalene sulfonates, alkyl phosphates, dialkyl sulfosuccinates, rosin soaps, and fatty acid salts (Na salts or amine salts). Examples of the usable nonionic surfactants include polyoxyethylene alkylphenol ethers, polyoxyethylene alkyl esters, polyoxyethylenealkylamines, polyoxyethylene alkyl ethers, polyoxyethylenealkylolamines, polyoxyethylenealkylamides, sorbitan alkyl esters, and polyoxyethylenesorbitan alkyl esters. Examples of the cationic surfactants which can be used include octadecylamine acetate, acetates of imidazoline derivatives, polyalkylenepolyamine derivatives or salts thereof, octadecyltrimethylammonium chloride, trimethylaminoethylalkylamide halides, alkylpyridinium sulfates, and alkyltrimethylammonium halogenides. A mixture of two or more of surfactants may be used. The surfactants, as well as the alcohols, decrease the surface tension of the processing liquid of the present invention, favorably disperse the colloidal silica in the processing liquid, and increase the affinity with the underlying coat.

In the second processing liquid of the present invention, usually 0.1 to 6.0% by mass of the colloidal silica, 2 to 10% by mass of the alcohol, and 0.01 to 0.5% by mass of the surfactant are included, the balance being water. If the content of the alcohol is less than 2% by mass, wettability of the antimicrobial composite material deteriorates, whereas if the content exceeds 10% by mass, volatility of the solvent becomes large to adversely affect coating operation. If the content of the surfactant is less than 0.01% by mass, the surface tension-lowering effect and colloidal silica-dispersing effect to be brought about by the surfactant become not remarkable, whereas if it is more than 0.5% by mass, the strength, water-resistance, durability and the like of the formed antimicrobial composite material are adversely affected.

[Method of Application of Processing Liquid]

After subjecting the surface of the substrate to coating operations to form an underlying layer, an intermediate layer, a top layer, and a clear layer thereon, the resulting coats are heated and dried usually at a temperature from 100 to 150° C. in a final drying step. After the final coat of the clear layer is heated and dried, the substrate is allowed to cool at a normal temperature. Application of the processing liquid is effected when the temperature of the coat lowered to desirably not more than 80° C., more desirably not more than 70° C. Below the above-mentioned temperature, there is no danger of the heat denaturation of the processing liquid. Usually the processing liquid is applied by spray coating, but other well known methods such as flow coater coating and roll coater coating are also applicable.

Although the amount of the processing liquid used for coating is not particularly restricted, the amount is usually such amount that the thickness of the layer of the processing liquid obtained by applying the processing liquid and drying becomes approximately 30 to 80 nm.

In the processing liquid, the colloidal silica is in the form of secondary fine particles in which several primary fine particles are associated and aggregated as mentioned above, and thus fine convexoconcaves are formed on the surfaces of the secondary particles. Accordingly, the antimicrobial composite material is captured by and adsorbed on the fine convexoconcaves on the surface of the colloidal silica. It is believed that the colloidal silica which absorbed the antimicrobial composite material is fixed to the surface of the coat (clear coat) on the substrate via hydrogen bonding.

The present invention will be explained below by way of specific embodiments.

At first, two kinds of solutions A and B which constitute a first processing liquid and a second processing liquid, respectively, are prepared.

A: Aqueous dispersion of colloidal silica.

4% by mass of colloidal silica (particle diameter of secondary particle: 50-100 nm), 4% by mass of ethanol, 0.25% by mass of a surfactant (polyoxyethylene alkyl phenol ether), and a balance (91.75% by mass) of water.

B: A solution in which kokinmaster (Idemitsu Technofine Co., Ltd., effective component: 20% by mass) is dispersed as an antimicrobial composite material in Solution A.

EXAMPLE 1

A pulp reinforced slag cement perlite board of 12 mm in thickness was sourced from Nichiha Corporation under the brand name Moen siding. The board was subjected to under coating, intermediate coating and top coating with an aqueous acrylic resin emulsion-type paint, and clear coating with an acrylic resin solution-type paint, and was heat-dried in a heating furnace at 100 to 110° C. for 20 minutes. After the heat-drying, the coated substrate was removed from the heating furnace, and allowed to cool at room temperature. When the surface temperature of the clear coat lowered to 65° C., solution B was applied by spray-coating, and then the coated substrate was allowed to stand at a normal temperature to dry the coat of the processing liquid by the remaining heat of the clear coat, thereby forming a covering layer containing the kokinmaster of 50 nm thick. Herein, a mixture of the aqueous dispersion of colloidal silica and the dispersion of kokinmaster in a ratio of 100:0.4 (dispersion) was applied in an amount of 40 g/m².

EXAMPLE 2

Except that a mixture of the aqueous dispersion of colloidal silica and the dispersion of kokinmaster in a ratio of 100:0.2 (dispersion) was used, the procedure of Example 1 was repeated.

EXAMPLE 3

Except that a mixture of the aqueous dispersion of colloidal silica and the dispersion of kokinmaster in a ratio of 100:0.1 (dispersion) was used, the procedure of Example 1 was repeated.

Comparative Example 1

The above-mentioned coated substrate in which the processing liquid was not applied, i.e. a coated pulp reinforced slag cement perlite board of 12 mm in thickness which had been subjected to usual coating, was used as a board of Comparative Example 1.

Comparative Example 2

The coated substrate to which a mixture of pure water and the dispersion of kokinmaster in a ratio of 100:0.4 (dispersion) had been applied in an amount of 40 g/m² was used as Comparative Example 2.

Test methods of algae resistance and fungi resistance according to Idemitsu system were carried out on the boards of Examples 1, 2 and 3, as well as Comparative Examples 1 and 2. The results obtained are shown in Tables 1 and 2.

(Test Methods)

As an antimicrobial performance test, algae or fungi were applied to the surface each of the coated building boards obtained in Examples 1, 2 and 3, as well as Comparative Examples 1 and 2, and algae resistance test was carried out according to the following test method.

(1) Tested fungi: Since algae generate on microorganisms, microorganisms (77 kinds of fungi) used for fungi resistance test and 27 kinds of algae were used as tested fungi (algae).

(2) Preparation of medium and test solution

Potato-Dextrose (PD) Agar Medium 39 g of a commercial dry medium (granule, Difco Laboratories) was distilled and sterilized with a high pressure steam at 121° C. for 15 minutes, and then dispensed to petri dishes for use.

(3) Incubation method and incubation conditions

Since algae generate and grow on microorganisms, 77 kinds of test fungi were sprinkled and then a suspension of 27 kinds of algae were sprinkled, and then test pieces of Examples 1, 2 and 3 and Comparative Examples 1 and 2 were put on the petri dishes, respectively, and incubation was effected.

Incubation conditions; temperature: 28-30° C., humidity: not less than 85% R.H., incubation period: 28 days. During incubation period, a sunlight fluorescent lamp of 1800 lux was irradiated for eight hours and the lamp was turned off for the remaining 16 hours in one day.

Fungi resistance test was carried out according to the following test method.

(1) Test fungi: 77 kinds of fungi consist of fungi that are said to exist in general housing and fungi that are detected in high ranks in life environment.

(2) Inorganic salt agar medium; 15 g of agar, 1000 ml of pure water and inorganic salts were subjected to sterilization treatment with heated steam at 121° C. for 120 minutes and then used.

(3) The tested fungi were added to an aqueous solution which has the same composition as that of the above-mentioned inorganic salt agar medium except that agar was excluded to adjust the number of tested fungi to $1\times10^6 \pm 2\times10^5$/ml, and the resulting aqueous solution was added to said inorganic salt agar medium in an equal amount, and then test pieces of Examples 1, 2 and 3 and Comparative Examples 1 and 2 were put on the petri dishes, respectively, and incubation was effected.

(4) Incubation was conducted for 28 days under the following incubation conditions: temperature of 28-30° C., humidity of not less than 85% R.H.

Evaluation criteria are as follows; 0: fungi do not grow at all, 1: growth of not more than 10%, 2: growth between 10% and not more than 30%, 3: growth between 30% and not more than 60%, 4: complete growth of not less than 60%.

(Carbon Contamination Test)

Silica sand incorporated with about 3 to 5% of carbon particle is applied to the surface coat of a coated building board with a tea spoon. Thereafter, water was applied thereto by means of an atomizer to wash away the silica sand. Then, stain-proofing property (hydrophilicity) can be confirmed by the degree of the adhesion of the carbon. Upon visual observation, the board from which the carbon was washed away was designated by ○, and that to which the carbon is partially adhered was designated by ×.

TABLE 1

| | Test results of the algae resistance test | | | | | | | |
|---|---|---|---|---|---|---|---|---|
| | Processing liquid | | | | | | | |
| | Aqueous dispersion of colloidal silica | Dispersion of kokinmaster | 7th day | 14th day | 21st day | 28th day | Surface judgment | Stain-proofing property |
| Example 1 | 4% of colloidal silica, 4% of ethanol, 0.25% of surfactant, and 91.75% of water | 0.40% | 0 | 0 | 0 | 0 | ○ | ○ |
| Example 2 | | 0.20% | 0 | 0 | 0 | 0 | ○ | ○ |
| Example 3 | | 0.10% | 0 | 0 | 0 | 0 | ○ | ○ |

TABLE 1-continued

Test results of the algae resistance test

| | Processing liquid | | | | | | | |
|---|---|---|---|---|---|---|---|---|
| | Aqueous dispersion of colloidal silica | Dispersion of kokinmaster | $7^{th}$ day | $14^{th}$ day | $21^{st}$ day | $28^{th}$ day | Surface judgment | Stain-proofing property |
| Comparative Example 1 | 0.0 | 0.0 | 0-1 | 2 | 3 | 3 | X | X |
| Comparative Example 2 | 0.0 | 0.40% | 0 | 0 | 0 | 0 | ○ | X |

TABLE 2

Test results of the fungi resistance test

| | Processing liquid | | | | | | | |
|---|---|---|---|---|---|---|---|---|
| | Aqueous dispersion of colloidal silica | Dispersion of kokinmaster | $7^{th}$ day | $14^{th}$ day | $21^{st}$ day | $28^{th}$ day | Surface judgment | Stain-proofing property |
| Example 1 | 4% of colloidal silica, | 0.40% | 0 | 0 | 0 | 0 | ○ | ○ |
| Example 2 | | 0.20% | 0 | 0 | 0 | 0 | ○ | ○ |
| Example 3 | 4% of ethanol, 0.25% of surfactant, and 91.75% of water | 0.10% | 0 | 0 | 0 | 0 | ○ | ○ |
| Comparative Example 1 | 0.0 | 0.0 | 0-1 | 2 | 3 | 3 | X | X |
| Comparative Example 2 | 0.0 | 0.40% | 0 | 0 | 0 | 0 | ○ | X |

From Tables 1 and 2, it was shown that, in the boards of Examples 2 and 3 in which the antimicrobial composite material contained in the kokinmaster liquid was coated in a lesser amount compared with Comparative Example 2, there was no generation of algae or fungi even after 28 days, carbon was washed away in the carbon contamination test and favorable algae resistance and fungi resistance were exhibited. On the other hand, in the board of Comparative Example 1 having no coating, algae and fungi generated and there was adhesion of stain in the carbon contamination test. In addition, in the board of Comparative Example 2 in which only the kokinmaster liquid was applied, no generation of algae and fungi was observed after 28 days, but adhesion of stain was observed in the carbon contamination test. It was experimentally proved and confirmed that only a small amount of an antimicrobial composite material was effective for preventing algae and fungi owing to the synergistic effects brought about in the examples while maintaining stain-proofing property.

INDUSTRIAL UTILIZATION

According to the present invention, it is possible to provide building boards with lasting and efficient effects of antimicrobial composite material, as well as with stain-proofing property.

What is claimed is:

1. A building board which has a coat containing colloidal silica as a main component and an antimicrobial composite material, said coat being formed on the board; wherein the antimicrobial composite material is a mixture of organic and inorganic antimicrobial agents.

2. The building board according to claim 1, wherein the antimicrobial composite material has a function to control generation of algae and fungi.

3. The building board according to claim 1 or 2, wherein the building board is a fiber reinforced cement board.

4. The building board according to claim 1, wherein the organic antimicrobial composite material comprises imidazole-based organic antimicrobial agents.

5. The building board according to claim 4, wherein the imidazole-based organic antimicrobial agents are selected from the group consisting of benzimidazole carbamic acid compounds, sulfur-containing benzimidazole compounds, and cyclic compound derivatives of benzimidazole.

6. The building board according to claim 1, wherein the organic antimicrobial agent is a combination of at least two imidazole-based organic antimicrobial agents.

7. The building board according to claim 4, wherein one of the imidazole-based organic antimicrobial agents is a compound having a thiazolyl-group on a benzimidazole ring and the other compound has a carbamate group on a benzimidazole ring.

8. The building board according to claim 1, wherein the inorganic antimicrobial agent comprises zirconium phosphate carrying silver or copper as a metal.

9. The building board according to claim 1, wherein the inorganic antimicrobial agent is a combination of silver supported zirconium phosphate and zinc oxide.

* * * * *